US007227027B2

(12) United States Patent
Qiu et al.

(10) Patent No.: US 7,227,027 B2
(45) Date of Patent: Jun. 5, 2007

(54) CARBAZOLE DERIVATIVE AND ITS USE IN ELECTROLUMINESCENT DEVICES

(75) Inventors: Yong Qiu, Beijing (CN); Juan Qiao, Beijing (CN); Jianhua Wang, Beijing (CN); Liduo Wang, Beijing (CN); Lian Duan, Beijing (CN); Gangtie Lei, Beijing (CN)

(73) Assignees: Tsinghua University, Beijing (CH); Beijing Visionox Technology Co., Ltd., Beijing (CH)

( * ) Notice: Subject to any disclaimer, the term of this patent is extended or adjusted under 35 U.S.C. 154(b) by 0 days.

(21) Appl. No.: 10/933,867

(22) Filed: Sep. 3, 2004

(65) Prior Publication Data

US 2005/0127826 A1 Jun. 16, 2005

(30) Foreign Application Priority Data

Sep. 5, 2003 (CN) .................................. 03156364

(51) Int. Cl.
    C07D 209/86 (2006.01)
    C07D 209/88 (2006.01)
(52) U.S. Cl. ........................ 548/440; 548/442; 548/445
(58) Field of Classification Search ................ 548/440, 548/442
    See application file for complete search history.

(56) References Cited

U.S. PATENT DOCUMENTS

| 6,303,238 B1 | 10/2001 | Thompson et al. | |
| 6,670,054 B1* | 12/2003 | Popovic et al. | 428/690 |
| 2004/0023060 A1* | 2/2004 | Kim et al. | 428/690 |

FOREIGN PATENT DOCUMENTS

| CN | 1365381 A | | 8/2002 |
| EP | 390551 A2 | * | 10/1990 |
| EP | 1 205 527 A1 | | 5/2002 |
| JP | 01234855 A2 | * | 9/1989 |
| JP | 07053681 A2 | * | 2/1995 |
| JP | 11008068 A2 | * | 1/1999 |
| JP | 11040359 A2 | * | 2/1999 |
| WO | WO200288274 A1 | * | 11/2002 |

OTHER PUBLICATIONS

Segal, et al. Proceedings of the SPIE-The International Society for Optical Engineering. 3796 (Organic Nonlinear Optical Materials), 153-159, Jul. 19, 1999.*
Sigalov, et al. Tetrahedron Letters. 41(44), 8573-8576, Oct. 28, 2000.*
D. Braun et al., "Synthesis and Characterization of Low Molecular Weight Organic Glasses," *J. Prakt. Chem.* 1999, 341, No. 2, pp. 128-137.
C. W. Tang et al., "Organic electroluminescent diodes," *Appl. Phys. Lett.* 51 (12), Sep. 21, 1987, pp. 913-915.
M. A. Baldo et al., "Highly efficient phosphorescent emission from organic electroluminiscent devices," *Nature*, vol. 395, Sep. 10, 1998, pp. 151-154.

D. F. O'Brien et al., "Improved energy transfer in electrophosphorescent devices," *Applied Physics Letters*, vol. 74, No. 3, Jan. 18, 1999, pp. 442-444.
Chihaya Adachi et al., "Endothermic energy transfer: A mechanism for generating very efficient high-energy phosphoresent emission in organic materials," *Applied Physics Letters*, vol. 79, No. 13, Sep. 24, 2001, pp. 2082-2084.
R. J. Holmes et al., "Blue organic electrophosphorescence using exothermic host-guest energy transfer," *Applied Physics Letters*, vol. 82, No. 15, Apr. 14, 2003, pp. 2422-2424.
Shizuo Tokito et al., "Confinement of triplet energy on phosphorescent molecules for highly-efficient organic blue-light-emitting devices," *Applied Physics Letters*, vol. 83, No. 3, Jul. 21, 2003, pp. 569-571.
Shoji Akai et al., "Tetrabutylammonium Nitrite—Acetic Anhydride System, Tetrabutylammonium Nitrite, Tetrabutylammonium Acetate, and Cesium Acetate—18-Crown-6 for Efficient unmasking of Alkyl N-Phenylcarbamates," *Tetrahedron Letters* 39 (1998) pp. 5583-5586.
Bryan E. Koene et al, "Asymmetric Triaryldiamines as Thermally Stable Hole Transporting Layers for Organic Light-Emitting Devices," *Chem. Mater.*, 1998, 10, pp. 2235-2250.

* cited by examiner

*Primary Examiner*—Joseph K. McKane
*Assistant Examiner*—Michael P. Barker
(74) *Attorney, Agent, or Firm*—RatnerPrestia

(57) ABSTRACT

The present invention relates to a series of carbazole derivatives which are used in organic electroluminescent devices as the phosphorescent host materials of the emissive layers. The carbazole derivatives have glass transition temperature of between 70° C. and 220° C. and triplet energy of 2.62 eV or more. The carbazole derivatives comprise two carbazole groups and alkyl group and/or spiro group inserted between the carbazole group and aromatic group, which is represented by formula 1. The carbazole derivatives according to the present invention are used as host materials for the triplet emissive dyes and they have high energy and stability. They can also reduce the converse energy transfer from the dye molecules to the host molecules and improve the luminance and efficiency of the OLEDs, especially the efficiency and lifetime of the blue triplet OLEDs.

(formula III)

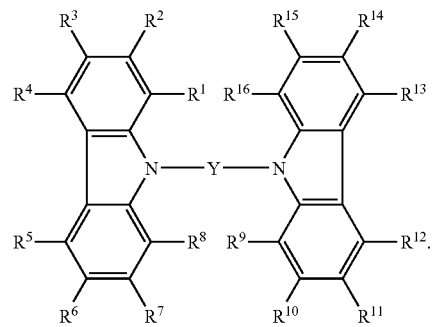

15 Claims, 1 Drawing Sheet

US 7,227,027 B2

CARBAZOLE DERIVATIVE AND ITS USE IN ELECTROLUMINESCENT DEVICES

This application claims priority to Chinese Patent Application No. 03156364.3, filed on Sep. 5, 2003.

BACKGROUND OF THE INVENTION

1. Field of the Invention

The present invention relates to a series of carbazole derivatives which can be used in organic electroluminescent devices as triplet host materials of the emissive layers.

2. Description of the Related Arts

With the development of the multimedia technology and the coming of the information society, the requirement to the flat panel display devices is higher and higher. The three kinds of new display technology, i.e. Plasma Display Panel (PDP), Field-Emission Display (FED) and Organic Light Emitting Devices (OLED), can surmount the shortcomings of the cathode ray tubes and liquid crystal display to a certain extent. The OLED has the properties of self-emission, low voltage DC driving, all-solid materials, wide visual angle and full color display, etc. Comparing to the LCD, the OLED doesn't need background illumination, has larger visual angle, costs less energy and its response speed is 1000 times more than that of the LCD while its cost is lower than that of LCD with the same resolution. So, OLED will have potential applications in many fields. In 1987, C. W. Tang et al of Kodak (C. W. Tang, S. A. Vanslyke, Appl. Phys. Lett., 1987, 51, 913) used 8-hydroxyquinoline aluminium ($Alq_3$) as the emitting layer and got an OLED having driving voltage of lower than 10V, luminescence of higher than 1000 $cd/m^2$ and the lifetime of more than 100 hours. OLED exhibits its potential practibility.

OLED works in accordance with the following mechanism: when a bias is applied across an anode and a cathode, electrons and holes are respectively injected from the anode and the cathode into the organic materials and then are transferred to the interface to combine and to form excitons which can emit light. OLED typically comprises a low-work-function cathode, a high-work-function anode and one or more layers of organic emissive material located between the anode and the cathode. The organic emissive layer may comprise at least one of electron-transporting layers, hole-transporting layers and emissive layers.

Although the research of OLED is developing rapidly, there are still some problems to be solved urgently and the most important one is that the quantum efficiency and stability of the devices can't reach application level. The EL quantum efficiency of the devices reflects the integration of all the factors and is an important index for evaluating quality of the devices. Generally, EL quantum efficiency of a device is represented by external quantum efficiency which is the fraction of the numbers of photons getting out of the devices and the numbers of carriers injected to the devices.

The OLED external quantum efficiency meets theoretically the following equation:

$$\eta_{qe} = \chi \Phi_F \eta_r \eta_e$$

wherein $\eta_{qe}$ is the external quantum efficiency, $\Phi_F$ is the intrinsic photoluminescent quantum efficiency of the emissive materials (including both fluorescence and phosphorescence) and ($\Phi_F \leq 1$, $\eta_r$ is the probability of the formation of excitons and $\eta_r \leq 1$, $\eta_e$ is the light out-coupling efficiency and $\eta_e \leq 1$, $\chi$ is the fraction of the formed total excitons which result in different radiative transitions and is about ¼ in relation to the singlet exitons while ¾ in relation to the triplet exitons. According to the above equation, the approaches of improving the external quantum efficiency of the devices may include: 1) using the emissive materials with high $\Phi_F$, 2) improving the probability of the formation of excitons, 3) improving the fraction of the photons getting out of the devices, and 4) improving the fraction of the available excitons.

Practically, the light out-coupling efficiency is up to 20%. The fluorescent molecular dyes can only use the singlet exitons and the external quantum efficiency of OLEDs is up to 5%. The triplet materials can use all of the formed exitons (both singlet and triplet exitons) and the external quantum efficiency of OLEDs can reach to 20%. So, use of the triplet emissive materials can improve the external quantum efficiency of OLEDs notably.

However, the triplet emissive materials have the triplet-triplet quenching when the concentration of triplet exitons is relatively high. So the triplet emissive materials should be doped into the host emissive materials instead of using itself alone as the emissive layers. In the energy transfer from the host to the guest materials, it requests the host materials have a higher energy level, so the host materials doped by the triplet emissive materials should have a higher triplet energy level.

Princeton University and University of Southern California worked together and in the U.S. Pat. No. 6,303,238 which was filed in December 1997 and published in October 2001 they first reported the triplet materials were used as the dopant to fabricate high efficiency OLEDs. This patent and other succeeding literatures written by the Forrest group from Princeton University (for example, M. A. Baldo, D. F. O'Brien, Y. You et al. Nature, 1998, 395, 151) published the research of using the triplet materials 2,3,7,8,12,13,17,18-octaethyl-21H,23H-porphine platinum (II) (PtOEP) as the guest emissive materials doped in $Alq_3$. Owing to the limit of spin-forbidden, the usage of excitons in fluorescent small molecule OLEDs is very low (the highest value is 25% in theory) and thus this limits the external quantum efficiency of fluorescent OLEDs (lower than 5%). On the other hand, if the triplet materials are used, the usage of excitons can reach 100% in theory and will improve the efficiency of the devices notably. Generally, the emission of the triplet materials at room temperature is quite low. However, PtOEP can emit phosphorescence at room temperature because the heavy metal Pt is introduced to the porphyrin rings and increases the rate of the intersystem crossing and the phosphorescence can be emitted at room temperature. The configuration of the device is represented as:

ITO/CuPc(6 nm)/NPB(35 nm)/$Alq_3$:PtOEP(6% wt,40 nm)/$Alq_3$(10 nm)/Mg:Ag(25:1, 100 nm)/Ag(50 nm)

Wherein CuPc is copper phthalocyanine, NPB is N,N'-bis(1-naphthyl)-N,N'-bis(phenyl)-benzidine, the device has an emissive peak at 650 nm at different current densities and has no peak at 580 nm while the PtOEP has a fluorescence peak at 580 nm and has a phosphorescence peak at 650 nm. This suggests that the emission of the device is originated from the phosphorescence of PtOEP. The internal quantum efficiency of the device reached as high as 23% at low luminescence and the external quantum efficiency was nearly 5%. However, the external quantum efficiency reduced to 1.3% at high luminescence (100 $cd/m^2$) and exhibited the emissive peak of $Alq_3$. This indicates that the energy transfer between the $Alq_3$ and PtOEP is not sufficient and the efficiency of the energy transfer is quite low.

In order to improve further the efficiency of the PtOEP phosphorescence devices, the Forrest group (D. F. O'Brien, M. A. Baldo, M. E. Thompson, S. R. Forrest, Appl. Phys.

Lett. 1999, 74, 442) substituted 4,4'-bis(9-carbazolyl)-2,2'-biphenyl (CBP, represented by formula I) for Alq$_3$ as the host material of the triplet dopant PtOEP, and introduced 2,9-dimethyl-4,7-diphenyl-1,10-phenanthroline (BCP) as the hole blocking layer after the emissive layer. The configuration of the device is represented as:

ITO/NPB(45 nm)/CBP:PtOEP(6%,40 nm)/BCP(8 nm)/Alq$_3$(25 nm)/Mg:Ag

It was found that the external quantum efficiency of the device was as high as 5.7%, and higher than the theoretical maximum 5%, which proved that the triplet emissive materials could gain higher efficiency. Comparing to Alq$_3$, CBP has higher triplet energy (CBP, 2.56 eV; Alq$_3$, 2.0 eV), the ability of ambipolar transfer. So it is more likely to reduce the back energy transfer from the dopant to the host materials and to increase the energy transfer from the triplet exitons of the host to the triplet emissive dopant materials. From then, CBP has been widely used as the host materials of many triplet emissive dopants and achieved high EL quantum efficiency for red, green, blue and white electrophosphorescence.

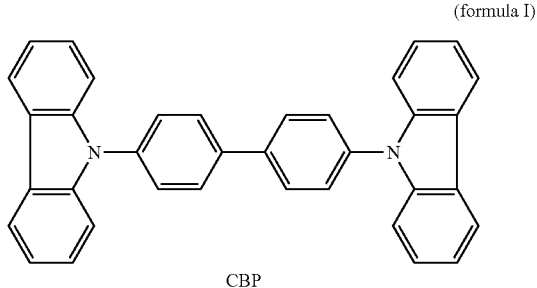

(formula I)

CBP

As the development of the research on phosphorescent electroluminescent devices, Princeton University and University of Southern California worked together to develop more and more triplet dopant with good performances. But the research on the host materials is relatively insufficient. The previous host materials used for fluorescent materials are not always suitable for the triplet emissive materials. So the research on the triplet emissive host materials is in great need.

The host materials for red or green triplet emissive materials are quite enough and CBP is the most-widely used materials. Some polymers such as polyvinylcarbazole (PVK) are also used as the host materials for the triplet dopant materials. But the host materials for blue triplet emissive dopants are rather few. For example, the commercially available blue triplet dopant material, iridium(III) bis[(4,6-difluorophenyl)-pyridinato-N,C$^{2'}$] picolinate (FIrpic, represented by the following formula II), was the first reported blue triplet emissive material and the emissive peak is at 475 nm at room temperature and the triplet energy level is 2.65 eV. However, the triplet energy level of the classic host material CBP is 2.56 eV. The Forrest group (Chihaya Adachi, Raymond C Kwong, et. al. Appl. Phys. Lett. 2001, 79,2082) used CBP as the host emissive materials of FIrpic and fabricated blue electroluminescent devices which have the external quantum efficiency of 5.7%, the maximum operation current density of 100 mA/cm$^2$ and the luminescence of only 6500 cd/m$^2$. The triplet energy level of CBP is lower than that of Firpic and the energy transfer from CBP to Firpic is an endothermic process. The efficiency of the endothermic transfer is very low and the energy transfer from the Firpic to CBP limits the efficiency and lifetime of the devices. In order to improve the efficiency and lifetime of the blue electroluminescent phosphorescent devices, the host materials with higher energy level are required.

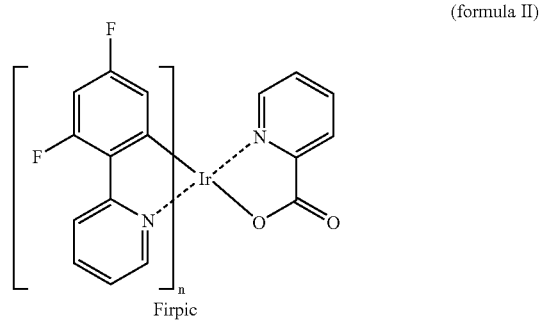

(formula II)

Firpic

The blue organic electroluminescent devices are absolutely necessary for the full-color display. So the blue electroluminescent devices with high efficiency and long lifetime are quite important. Both the theoretical research and the experimental records proved that the triplet emissive materials are helpful to improve the EL efficiency of the OLEDs. Developing host emissive materials with high energy level for blue triplet emissive materials is a hot and challenging subject matter.

Recently, the Forrest group (R. J. Holmes, S. R. Forrest, et al. Appl. Phys. Lett. 2003, 82, 2422) reported a new type of carbazole derivative, N,N-'-dicarbazolyl-3,5-benzene (mCP), of which the triplet energy is 2.90 eV. After using mCP as the host emissive materials and Firpic as the dopant, the maximum external quantum efficiency of the device was 7.5% and it was 30% higher than the device used CBP as the host emissive materials. That was because the energy transfer from mCP to Firpic is an exothermic process and the energy transfer was more efficient. Later, Tokito et al (Shizuo Tokito, Toshiki Lijima, et al. Appl. Phys. Lett. 2003, 83, 569) reported a type of CBP substituted by two methyls, 4,4'-bis(9-carbazolyl)-2,2'-dimethyl-biphenyl (CDBP), with the triplet energy level of 3.0 eV, and the external quantum efficiency of the device doped with Firpic was as high as 10.4%.

Both mCP and CDBP have higher triplet energy than the blue triplet dopant FIrpic (2.65 eV). As a result, the devices using mCP and CDBP as host materials and using Firpic as dopant gained high quantum efficiency. But the thermal stability and the film-forming capability of the mCP and CDBP are quite low. The glass transition temperature of mCP is only 65° C. and the organic emissive layer is easy to crystallize. Furthermore, the maximum operation current density is only 100 mA/cm$^2$ and the higher driving current will damage the devices. So, in the search of the host material with high energy, the thermal stability is also considered. In the Chinese patent application publication No. CN1365381A, a series of carbazole derivatives were designed, which have the glass transition temperature of above 110° C. and the triplet energy of above 21000 m$^{-1}$ (2.56 eV, according to the wavelength at 488 nm). These carbazole derivatives were used as dopants in the OLEDs with the triplet emissive dyes. These carbazole derivatives comprise a triphenylamine group directly linked to the aromatic group as the center unit or carbazole oligomer. It was discovered from the preferred structures that along with the number of repeated aromatic groups increase, the conjugation of the molecule increase so that the triplet energy would reduce.

SUMMARY OF THE INVENTION

An object of the present invention is to provide a series of carbazole derivatives having high triplet energy and stability, which are usable in the emissive layers of OLEDs as host materials for triplet emissive dyes. The efficiency and lifetime of the OLEDs (especially the blue triplet OLEDs) can be improved by reducing the converse energy transfer from the guest molecules to the host molecules.

The series of carbazole derivatives comprise two carbazole groups, and are represented by the formula (III):

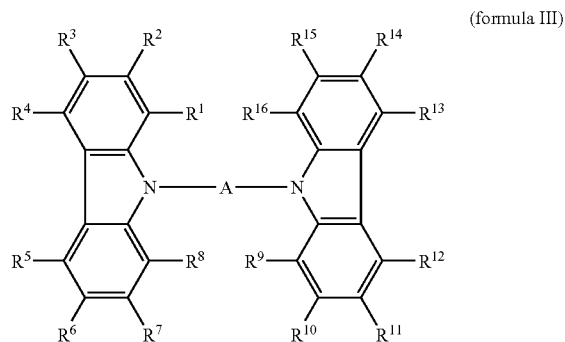

(formula III)

wherein Y is selected from alkyl group linked to aromatic group, alkyl group linked to spiro group, aromatic group linked to spiro group, alkyl and aromatic group linked to alkenyl group, as well as alkyl and aromatic group linked to spiro group, $R^1$ to $R^{16}$ are independently selected from the group consisting of H, alkyl group, alkoxy group, aromatic group, fluoroalkyl group, halogen, and cyanic group.

The carbazole derivatives according to the invention preferably have glass transition temperature of between 70° C. and 220° C. and triplet energy of 2.62 eV or more.

In one embodiment of formula (III), Y is C1 to C3 alkyl group linked to C6 to C50 aromatic group.

In further embodiment of formula (III), Y is alkyl having 1–3 carbon atoms and aromatic group having 6–50 carbon atoms, which is linked to alkenyl group.

In further embodiment of formula (III), Y is C1 to C3 alkyl group linked to spiro group.

In further embodiment of formula (III), Y is nonplanar C6 to C50 aromatic group (substituted or unsubstituted) linked to spiro group.

In further embodiment of formula (III), Y is nonplanar C1 to C3 alkyl and nonplanar C6 to C50 aromatic group (substituted or unsubstituted) linked to spiro group.

In further embodiment of formula (III), the spiro group of Y is substituted by alkyl group, aromatic group, or halogen.

This invention provides also an organic electroluminescent device comprising an anode layer, a cathode layer, and an organic emissive layer between the anode layer and the cathode layer, wherein the organic emissive layer comprises the carbazole derivatives represented by formula (III) and a triplet dopant.

In formula (III), when Y is alkyl group linked to aromatic group, the preferred examples of carbazole derivatives include those compounds represented by the following formulae 2–26:

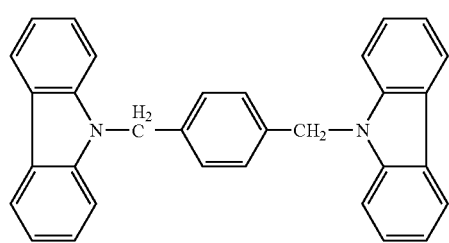
(2)

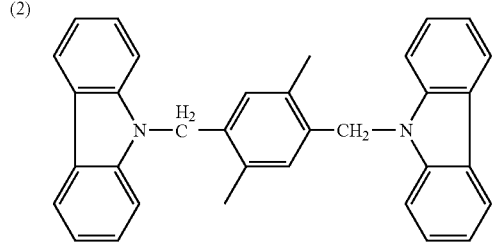
(3)

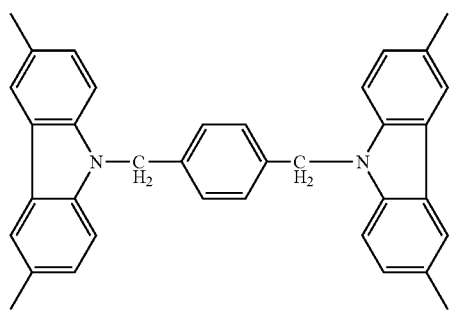
(4)

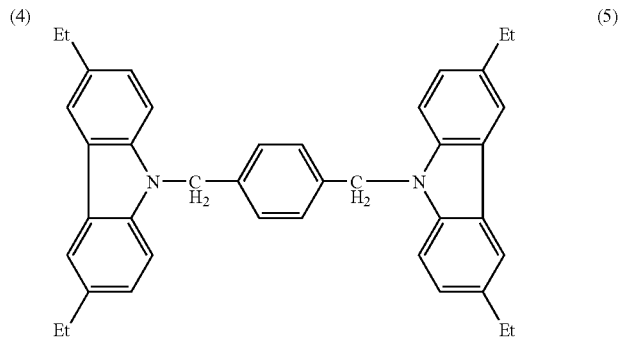
(5)

-continued
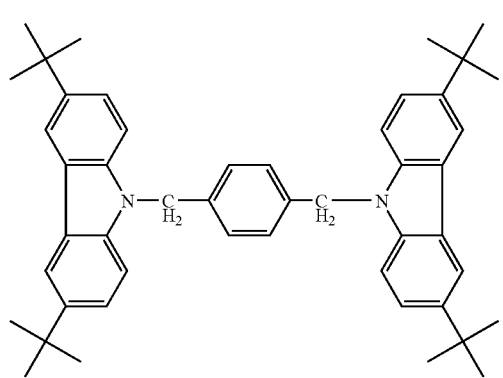
(6)
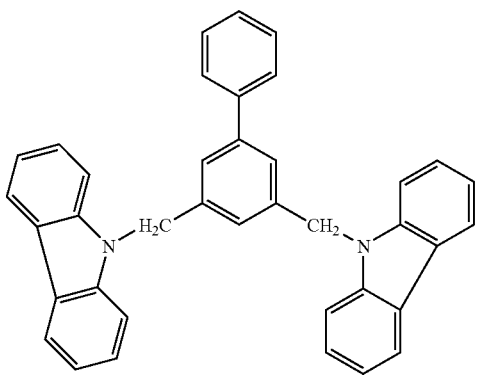
(7)
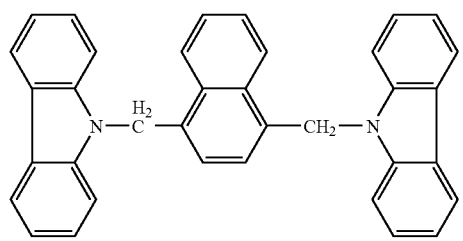
(8)
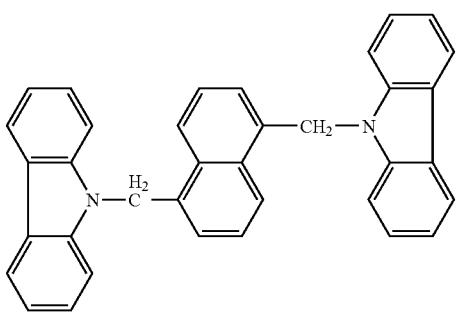
(9)
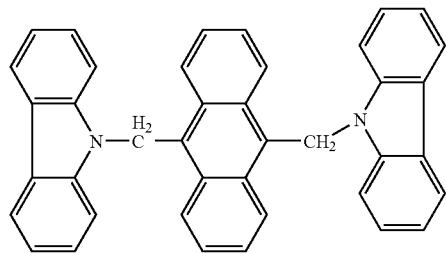
(10)
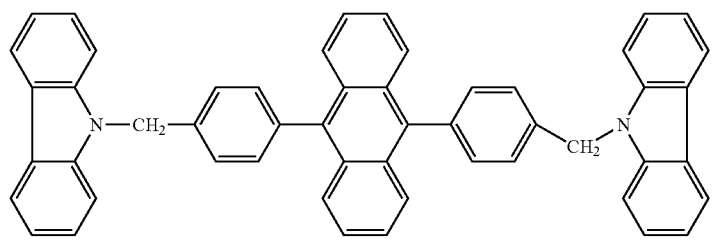
(11)
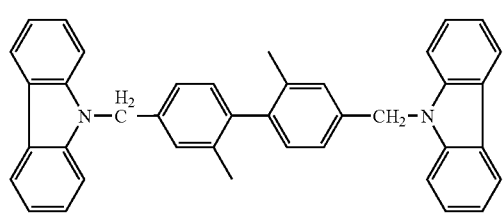
(12)
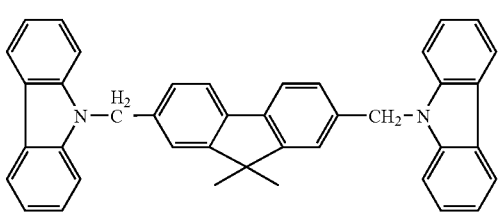
(13)

-continued
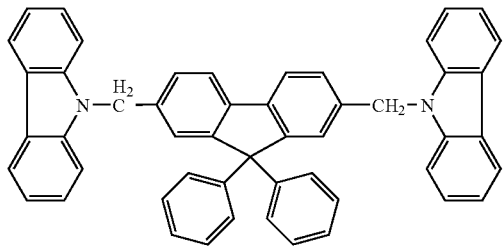
(14)
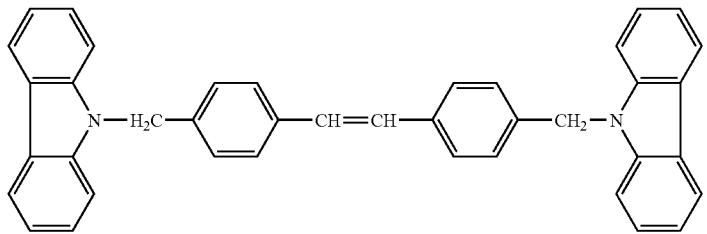
(15)
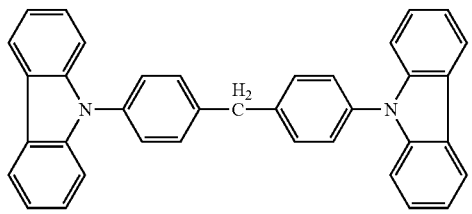
(16)
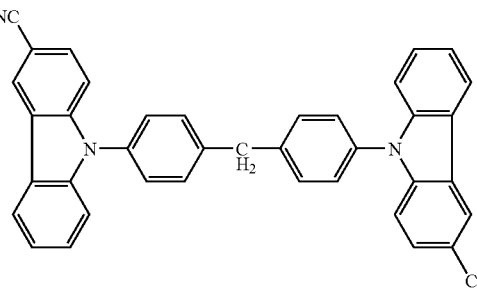
(17)
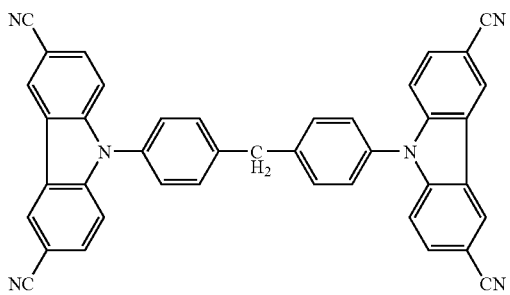
(18)
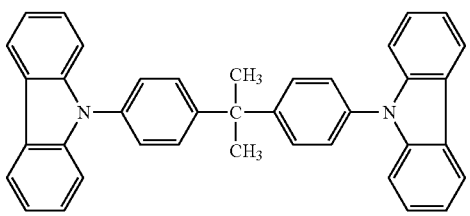
(19)
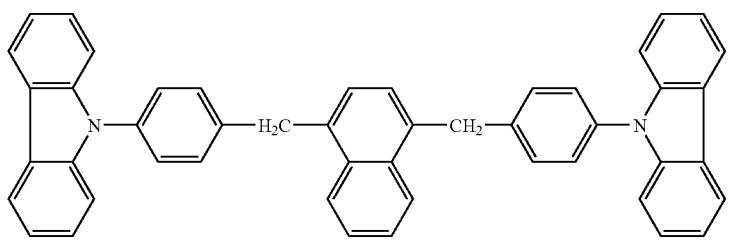
(20)
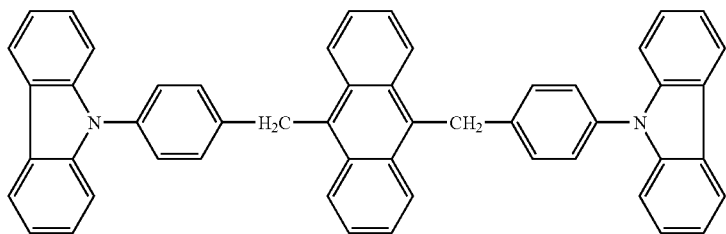
(21)

-continued
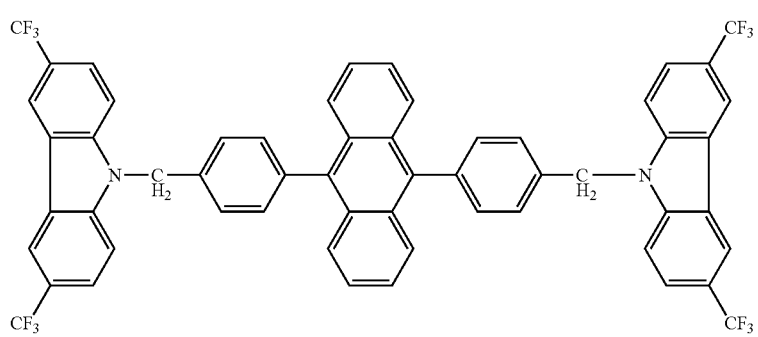
(22)
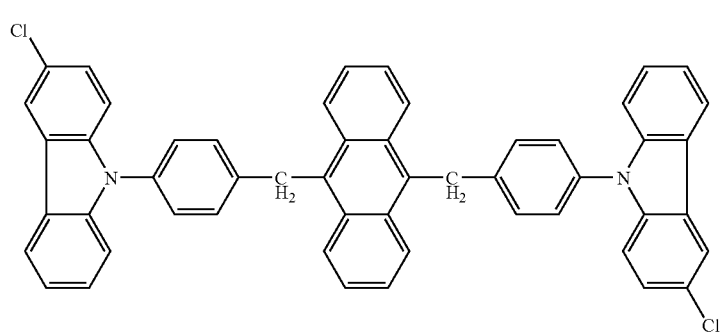
(23)
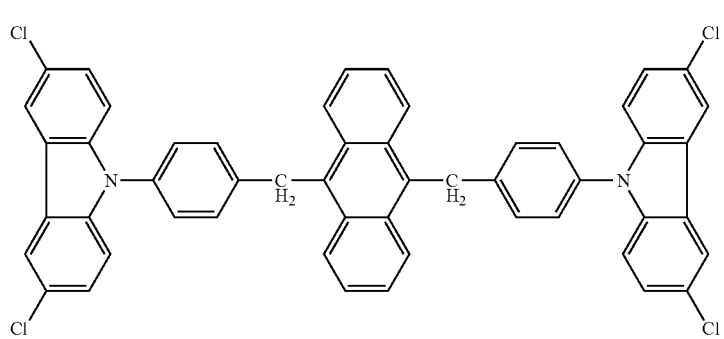
(24)
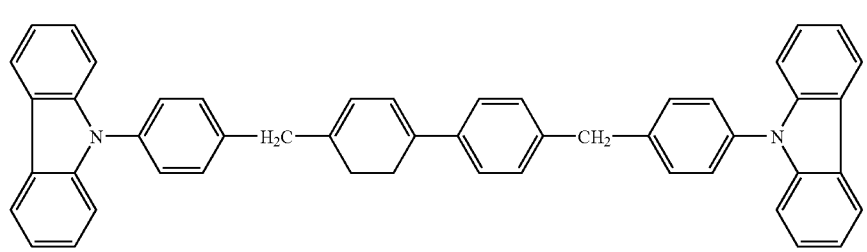
(25)
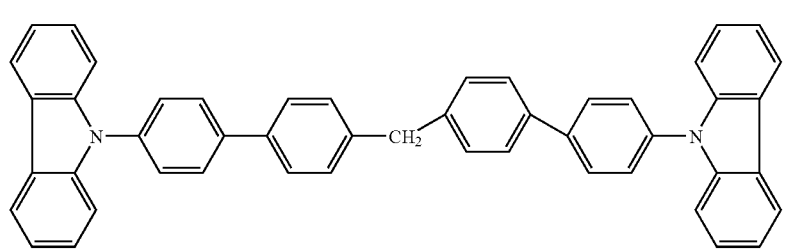
(26)

In formula (III), when Y is alkyl group linked to Spiro group, aromatic group linked to spiro group or alkyl or aromatic group linked to Spiro group, the preferred examples of carbazole derivatives include those compounds represented by the following formulae 27–34:
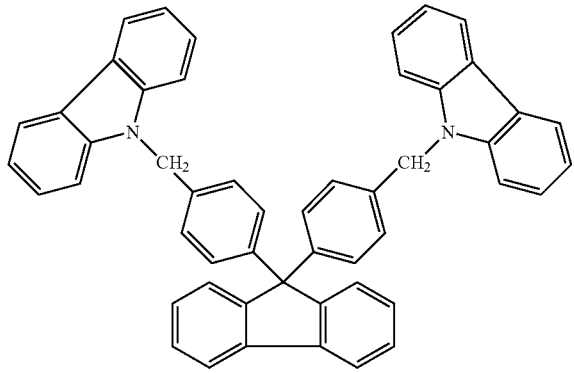
(27)
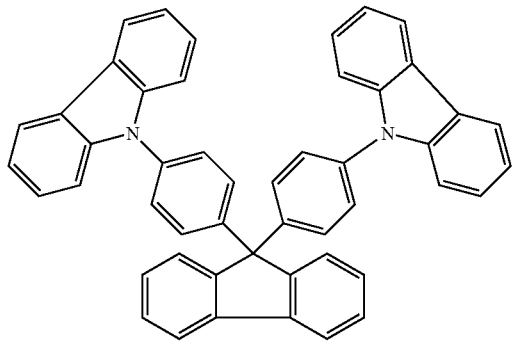
(28)
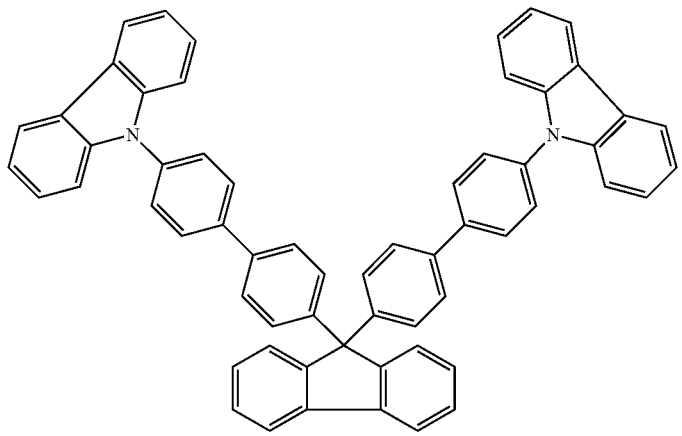
(29)

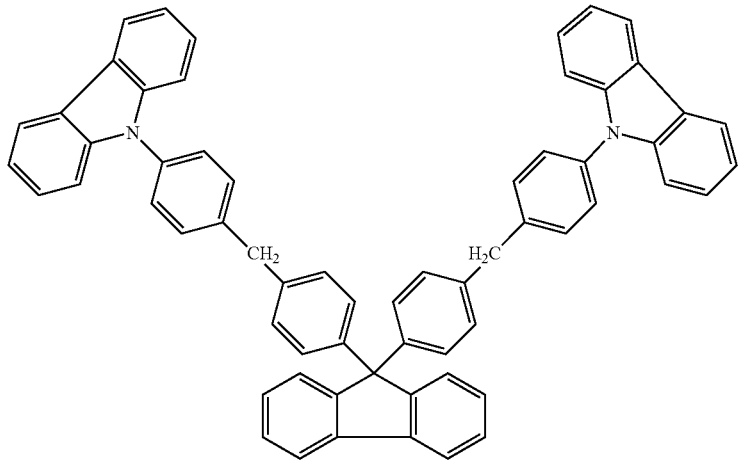
(30)
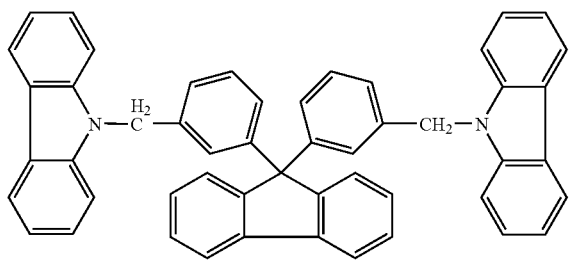
(31)
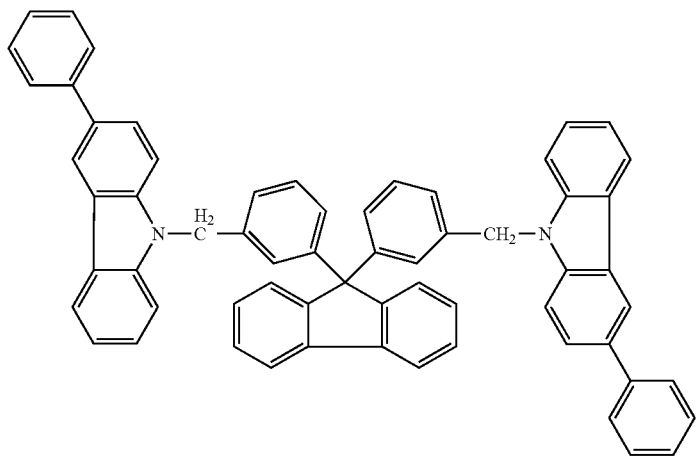
(32)
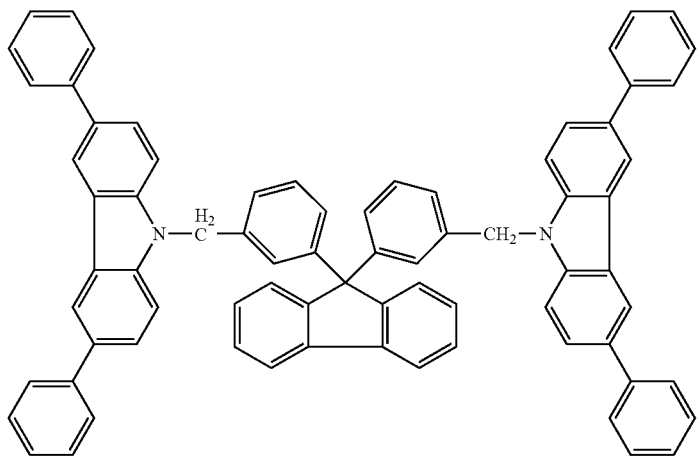
(33)

-continued (34)

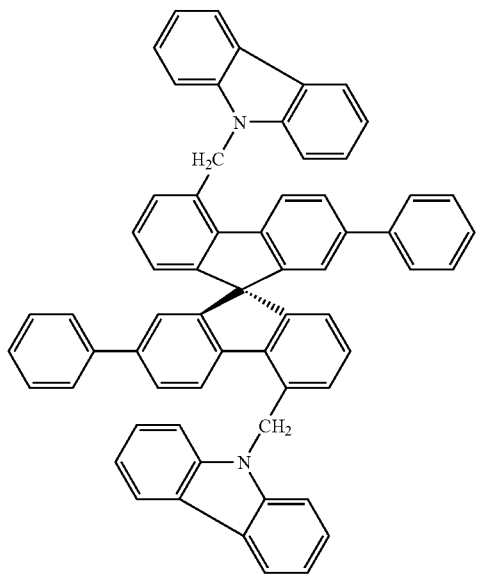

The present invention aims to design the carbazole derivatives with high energy and stability. The structural characteristic of the carbazole derivatives is that the carbazole derivatives comprise two carbazole groups, and alkyl group and/or spiro group inserted between the carbazole group and an aromatic group, which could reduce the conjugation of the aromatic group and the carbazole group, therefore the triplet energy level will be heightened and the ability of forming films will be improved as well.

The carbazole derivatives designed according to the present invention have the triplet energy of higher than 21050 cm$^{-1}$ (while the triplet energy of the blue triplet dopant Firpic is 2.62V and the emissive wavelength is at 475 nm). These carbazole derivatives have excellent features as follows: having triplet energies T1 of 2.62 eV or more, rather high glass transition temperatures (70° C.–220° C.) as well as good thermal stability and being easy to form amorphous thin films. For example, the preferred compound No. 20, 9,9'-N,N'-(4-dicarbazol-phenyl) fluorene (CPF), has triplet energy of 2.88 eV which is higher than that of Firpic by 0.26 eV and has phosphorescent wavelength of 432 nm and. This material possesses extremely high thermal stability, having glass transition temperature of 165° C. and melting point of 405° C.

The OLEDs using the carbazole derivatives of the present invention as the host materials exhibit high luminescence and high efficiency. If we record the triplet energy of these carbazole derivatives as T1(Carbazole), the triplet energy of the triplet dyes as T1(Ph-dye), and so there is T1(Carbazole)>T1(Ph-dye). This means that the triplet energy of the carbazole derivatives will transfer to the triplet dyes efficiently and we can gain high efficiency OLEDs even at room temperature.

It was found that by choosing the proper triplet dyes, we can easily gain the high efficient emission of red, green, yellow, blue and other colors. The available triplet dyes include the heavy metal complexes of Ir, Pt, Os, Ru, Re, Pd and so on. The preferred complex of Ir and Pt, such as blue material iridium(III)bis[(4,6-difluorophenyl)-pyridinato-N,C-2']picolinate (FIrpic), green material tri-(2-phenylpyridinato-N,C$^{2'}$)iridium (Ir(ppy)$_3$), green material bis-(2-phenylpyridinato-N,C$^2$) iridium(acetylacetonate) (Ir(ppy)$_2$ (acac)), red material 2,3,7,8,12,13,17,18-octaethyl-21H, 23H-porphine platinum(II) (PtOEP) are respectively represented by the following structures:

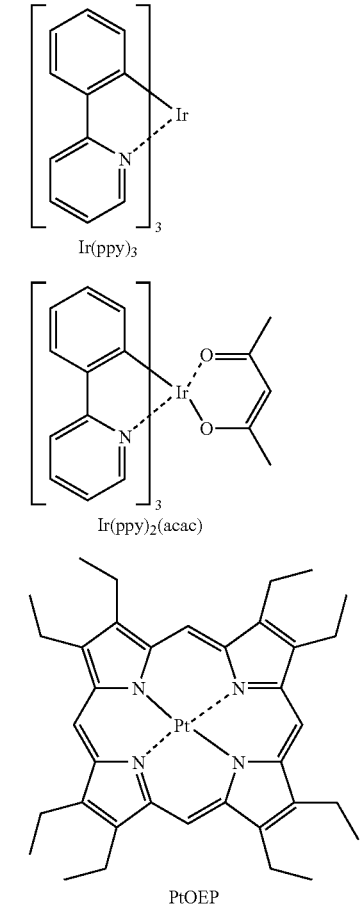

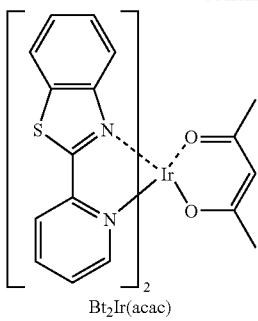

Bt₂Ir(acac)

Amount of the doped triplet dyes is 0–100 g and preferably is 3–20 g per 100 g carbazole derivatives as the host materials. By using the carbazole derivatives of formula 2, DCB and formula 20, CPF doped with 6% or 8% blue dyes Firpic, we can obtain high luminescence and high efficiency blue phosphorescent devices, which have better performance than those of the devices using CBP as the host material. Furthermore, these materials can be used with fluorescent dyes or without any dyes to fabricate OLEDs.

DETAILED DESCRIPTION OF THE INVENTION

EXAMPLE 1

Figure 1:
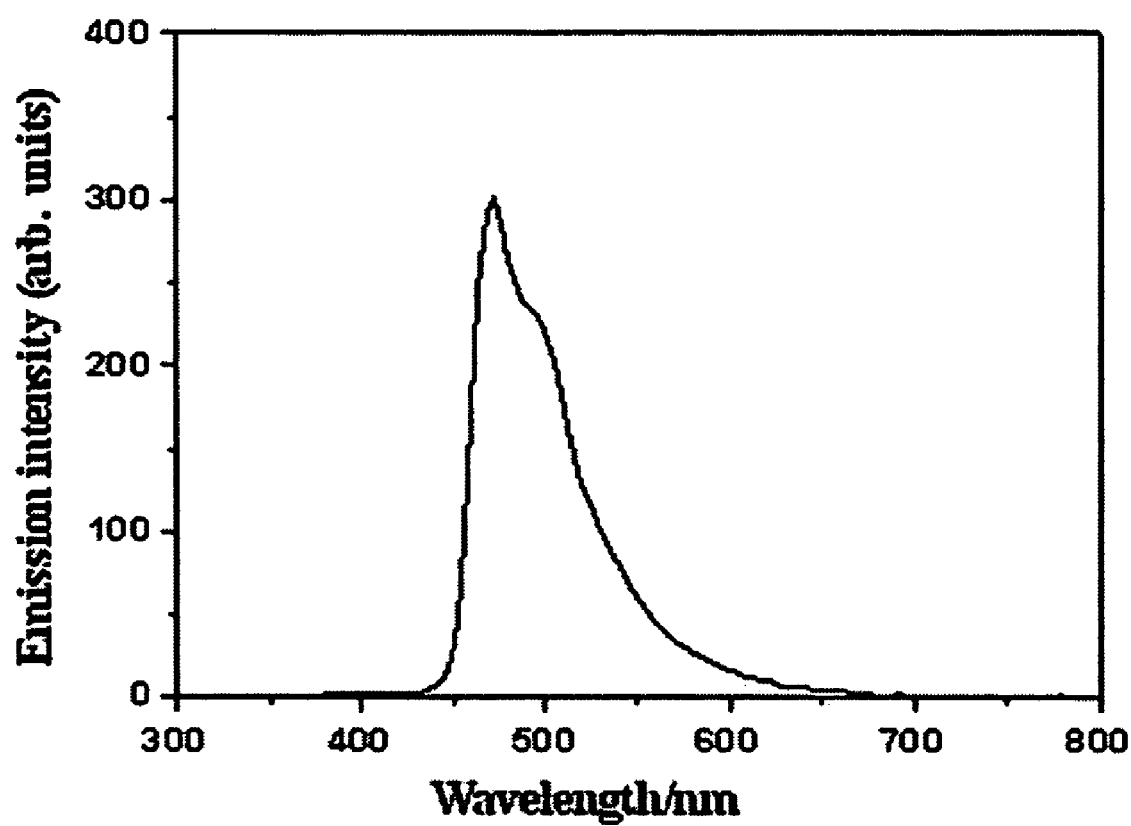
FIG. 1 is a graph showing the emissive spectra of the devices with the compound according to formula 27 doped with Firpic.

Synthesis of
N,N'-Dicarbazolyl-1,4-Dimethylene-Benzene
(Compound No. 2)

The compound were synthesized by the condensation reaction of aromatic halides and carbazole according to the method reported in the literature (T. Yamamoto, et al. Tetrahedron Lett. 1998, 84, 5583.; B. K. Koene, et al. Chem. Mater. 1998, 10, 2235): 5.01 g (0.03 mol) carbazole was dissolved in 100 ml absolute THF to form a solution, then 0.72 g (0.03 mol) NaH was added very gradually to the solution. When the hydrogen was exhausted, 1.75 g (0.01 mol) 1,4-Bis-chloromethyl-benzene was added, then refluxed for 24 h, the mixture was cooled to room temperature, filtered and gave 3.62 g white solid with yield of 80%. The resulting product was identified to be compound No. 2 according to the following data. Mass spectrum: m/e=436. Chemical analysis: Found [C(88.12%), H(5.39%), N(6.50%)]; Calcd [C(88.07%), H(5.50%), N(6.42%)].

EXAMPLE 2

Synthesis of Compound No. 3

Compound No. 3 was synthesized in the same manner as compound No. 2, except substituting 1,4-Bis-chloromethyl-2,5-dimethyl-benzene for 1,4-Bis-chloromethyl-benzene. Yield was 78%. Mass spectrum: m/e=464. Chemical analysis: Found [C(88.05%), H(5.99%), N(6.13%)]; Calcd [C(87.93%), H(6.03%), N(6.03%)].

EXAMPLE 3

Synthesis of Compound No. 4

Compound No. 4 was synthesized in the same manner as compound No. 2, except substituting 3,6-Dimethyl-9H-carbazole for carbazole. Yield was 64%. Mass spectrum: m/e=492. Chemical analysis: Found [C(87.65%), H(6.53%), N(5.62%)]; Calcd [C(87.77%), H(6.55%), N(5.69%)].

EXAMPLE 4

Synthesis of Compound No. 5

Compound No. 5 was synthesized in the same manner as compound No. 2, except substituting 3,6-Diethyl-9H-carbazole for carbazole. Yield was 66%. Mass spectrum: m/e=548. Chemical analysis: Found [C(87.59%), H(7.42%), N(5.07%)]; Calcd [C(87.55%), H(7.35%), N(5.10%)].

EXAMPLE 5

Synthesis of Compound No. 6

Compound No. 6 was synthesized in the same manner as compound No. 2, except substituting 3,6-Di-tert-butyl-9H-carbazole for carbazole. Yield was 62%. Mass spectrum: m/e=660. Chemical analysis: Found [C(87.34%), H(8.53%), N(4.33%)]; Calcd [C(87.22%), H(8.54%), N(4.24%)].

EXAMPLE 6

Synthesis of Compound No. 7

Compound No. 7 was synthesized in the same manner as compound No. 2, except substituting 3,5-Bis-chloromethyl-biphenyl for 1,4-Bis-chloromethyl-benzene. Yield was 68%. Mass spectrum: m/e=512. Chemical analysis: Found [C(89.12%), H(5.53%), N(5.39%)]; Calcd [C(89.06%), H(5.47%), N(5.47%)].

EXAMPLE 7

Synthesis of Compound No. 8

Compound No. 8 was synthesized in the same manner as compound No. 2, except substituting 1,4-Bis-chloromethyl-naphthalene for 1,4-Bis-chloromethyl-benzene. Yield was 68%. Mass spectrum: m/e=486. Chemical analysis: Found [C(88.92%), H(5.42%), N(5.64%)]; Calcd [C(88.89%), H(5.35%), N(5.76%)].

EXAMPLE 8

Synthesis of Compound No. 9

Compound No. 9 was synthesized in the same manner as compound No. 2, except substituting 1,5-Bis-chloromethyl-naphthalene for 1,4-Bis-chloromethyl-benzene. Yield was 75%. Mass spectrum: m/e=486. Chemical analysis: Found [C(88.94%), H(5.39%), N(5.61%)]; Calcd [C(88.89%), H(5.35%), N(5.76%)].

EXAMPLE 9

Synthesis of Compound No. 10

Compound No. 10 was synthesized in the same manner as compound No. 2, except substituting 9,10-Bis-chloromethyl-anthracene for 1,4-Bis-chloromethyl-benzene. Yield was 70%. Mass spectrum: m/e=536. Chemical analysis: Found [C(89.75%), H(5.16%), N(5.32%)]; Calcd [C(89.55%), H(5.22%), N(5.22%)].

EXAMPLE 10

Synthesis of Compound No. 11

Compound No. 11 was synthesized in the same manner as compound No. 2, except substituting 9,10-Bis-(4-chloromethyl-phenyl)-anthracene for 1,4-Bis-chloromethyl-benzene. Yield was 77%. Mass spectrum: m/e=688. Chemical analysis: Found [C(90.85%), H(5.12%), N(3.96%)]; Calcd [C(90.70%), H(5.23%), N(4.07%)].

EXAMPLE 11

Synthesis of Compound No. 12

Compound No. 12 was synthesized in the same manner as compound No. 2, except substituting 4,4'-Bis-chloromethyl-2,2'-dimethyl-biphenyl for 1,4-Bis-chloromethyl-benzene. Yield was 77%. Mass spectrum: m/e=540. Chemical analysis: Found [C(88.95%), H(5.95%), N(5.06%)]; Calcd [C(88.99%), H(5.93%), N(5.19%)].

EXAMPLE 12

Synthesis of Compound No. 13

Compound No. 13 was synthesized in the same manner as compound No. 2, except substituting 2,7-Bis-chloromethyl-9,9-dimethyl-9H-fluorene for 1,4-Bis-chloromethyl-benzene. Yield was 75%. Mass spectrum: m/e=552. Chemical analysis: Found [C(88.99%), H(5.75%), N(5.13%)]; Calcd [C(89.13%), H(5.80%), N(5.07%)].

EXAMPLE 13

Synthesis of Compound No. 14

Compound No. 14 was synthesized in the same manner as compound No. 2, except substituting 2,7-Bis-chloromethyl-9,9-diphenyl-9H-fluorene for 1,4-Bis-chloromethyl-benzene. Yield was 77%. Mass spectrum: m/e=676. Chemical analysis: Found [C(90.39%], H(5.19%), N(4.23%)); Calcd [C(90.53%), H(5.33%), N(4.14%)].

EXAMPLE 14

Synthesis of Compound No. 15

Compound No. 15 was synthesized in the same manner as compound No. 2, except substituting 4,4'-Bis-chloromethyl-distyrene for 1,4-Bis-chloromethyl-benzene. Yield was 65%. Mass spectrum: m/e=538. Chemical analysis: Found [C(89.15%), H(5.53%), N(5.26%)]; Calcd [C(89.22%), H(5.58%), N(5.20%)].

EXAMPLE 15

Synthesis of Compound No. 16

Compound No. 16 was synthesized by the Ullman condensation reaction under the catalyst copper according to the reported literature (B. K. Koene, et al. Chem. Mater. 1998, 10, 2235): a round-bottomed flask was charged with Cu (1.0 equiv), 18-crown-6 (0.15 equiv), and $K_2CO_3$ (2 equiv). O-dichlorobenzene, Bis-(4-iodo-phenyl)methane (1.0 equiv) and carbazole (2.1 equiv) were added under a stream of nitrogen. The mixture was heated to 180–200° C. for 16–48 h. At end of the reaction, the mixture was filtered immediately through silica. Yield was 82%. Mass spectrum: m/e=498. Chemical analysis: Found [C(89.36%), H(5.15%), N(5.72%)]; Calcd [C(89.16%), H(5.22%), N(5.62%)].

EXAMPLE 16

Synthesis of Compound No. 17

Compound No. 17 was synthesized in the same manner as compound No. 16, except substituting 9H-Carbazole-3-carbonitrile for carbazole. Yield was 69%. Mass spectrum: m/e=548. Chemical analysis: Found [C(85.36%), H(4.38%), N(10.18%)]; Calcd [C(85.38%), H(4.41%), N(10.21%)].

EXAMPLE 17

Synthesis of Compound No. 18

Compound No. 18 was synthesized in the same manner as compound No. 16, except substituting 9H-Carbazole-3,6-dicarbonitrile for carbazole. Yield was 58%. Mass spectrum: m/e=598. Chemical analysis: Found [C(82.33%), H(3.75%), N(13.99%)]; Calcd [C(82.26%), H(3.70%), N(114.04%)].

EXAMPLE 18

Synthesis of Compound No. 27

Compound No. 27 was synthesized in the same manner as compound No. 16, except substituting 9,9-Bis-(4-iodo-phenyl)-9H-fluorene for Bis-(4-iodo-phenyl)methane. Yield was 65%. Mass spectrum: m/e=648. Chemical analysis: Found [C(90.65%), H(4.52%), N(4.46%)]; Calcd [C(90.74%), H(4.94%), N(4.32%)].

EXAMPLE 19

Synthesis of Compound No. 28

Compound No. 28 was synthesized in the same manner as compound No. 2 except substituting 9,9-Bis-(4-chloromethyl-phenyl)-9H-fluorene for 1,4-Bis-chloromethyl-benzene. Yield was 68%. Mass spectrum: m/e=676. Chemical analysis: Found [C(90.49%), H(5.53%), N(4.22%)]; Calcd [C(90.53%), H(5.33%), N(4.14%)].

EXAMPLE 20

Synthesis of Compound No. 29

Compound No. 29 was synthesized in the same manner as compound No. 27, except substituting 9,9-Bis-(4'-iodo-biphenyl-4-yl)-9H-fluorene for 9,9-Bis-(4-iodo-phenyl)-9H-fluorene. Yield was 66%. Mass spectrum: m/e=800. Chemical analysis: Found [C(91.65%), H(4.95%), N(3.46%)]; Calcd [C(91.50%), H(5.00%), N(3.50%)].

EXAMPLE 21

Synthesis of Compound No. 31

Compound No. 31 was synthesized in the same manner as compound No. 2, except substituting 2,7-Bis-chloromethyl-9,9'-spirobisfluorene for 1,4-Bis-chloromethyl-benzene. Yield was 75%. Mass spectrum: m/e=674. Chemical analysis: Found [C(90.59%), H(5.25%), N(4.22%)]; Calcd [C(90.77%), H(5.08%), N(4.15%)].

EXAMPLE 22

Synthesis of Compound No. 32

Compound No. 32 was synthesized in the same manner as compound No. 14, except substituting 3-Phenyl-9H-carbazole for carbazole. Yield was 62%. Mass spectrum: m/e=828. Chemical analysis: Found [C(91.35%), H(5.34%), N(3.19%)]; Calcd [C(91.49%), H(5.12%), N(3.39%)].

EXAMPLE 23

Synthesis of Compound No. 33

Compound No. 33 was synthesized in the same manner as compound No. 14, except substituting 3,6-Diphenyl-9H-carbazole for carbazole. Yield was 55%. Mass spectrum: m/e=980. Chemical analysis: Found [C(91.68%), H(5.38%), N(2.72%)]; Calcd [C(91.80%), H(5.34%), N(2.85%)].

Fabrication of the OLEDs

The carbazole derivatives can be used as host materials and doped triplet dyes to fabricate OLEDs with high luminance and efficiency. When the triplet energy level is proper for the blue triplet dyes, there will be high efficient and stable blue phosphorescent emission. The typical devices are represented as:

anode (ITO)/hole transport layer (HTL)/doped emissive layer (carbazole derivatives: triplet dyes)/hole blocking layer (HBL)/electron transport layer (ETL)/cathode (metal).

(1) Hole injection and transport layer: the thickness is generally about 5 nm–5 μm. The preferred compounds include phthalocyanines and aromatic amine. The most typical materials are N,N'-biphenyl-N, N'-bis(1-naphthyl)-benzidine (NPB), N,N'-diphenyl-N,N'-bis(3-methylphenyl)-benzidine (TPD) or 4,4',441 -tris(3-methylphenyl-phenylamino)-triphenylamine (m-MTDATA).

(2) Hole blocking layer: The preferred hole blocking materials are 2,9-dimethyl-4,7-diphenyl-1,10-phenanthroline (BCP) and 4,7-diphenyl-1,10-phenanthroline (BPhen).

(3) Electron injection and transport layer: 8-hydroxyquinoline aluminum ($Alq_3$) and its derivatives can be used as electron injection and transport layer while the materials used for hole-blocking layer can also be used as electron injection and transport layer.

EXAMPLE 24

A blue OLED was fabricated by using compound No. 2 (DCB) as the host material and blue triplet dye Firpic as the dopant. The fabrication includes: on a clean glass substrate coated with ITO, 40 nm NPB as the hole transport layer and compound No. 2 doped with 8% (by weight) Firpic as the emissive layer were deposited by a vacuum vapor deposition, then the 30 nm hole blocking and electron transport layer Bphen and 200 nm metal of Mg:Ag (10:1) as cathode were further deposited by a vacuum vapor deposition.

The configuration of the device is: ITO/NPB(40 nm)/compound No. 2:Firpic(8%) (x nm)/Bphen(30 nm)/Mg:Ag.

Four devices are fabricated similarly by only altering the thickness of the emissive layer to 50, 40, 30 and 20 nm. Their performances were shown in table 1.

TABLE 1 the performance of the devices ITO/NPB(40 nm)/DCB(x nm) + FIrpic (8 wt. %)/Bphen(30 nm)/Mg:Ag

| | thickness of the emissive layer (nm) | | | |
|---|---|---|---|---|
| | 50 | 40 | 30 | 20 |
| EL efficiency (cd/A) | 8.7 | 9.0 | 9.8 | 8.0 |
| driving voltage (V) | 5.3 | 5.0 | 4.8 | 4.1 |
| luminance (cd/m$^2$) | 16480 | 16420 | 14000 | 12700 |

EXAMPLE 25

A blue OLED was fabricated in the same manner as in Example 24, except using compound No. 4 as the host material and blue triplet dye Firpic as the dopant. The configuration of the device is: ITO/NPB(40 nm)/compound No. 4:Firpic (8%) (30 nm)/Bphen(30 nm)/Mg:Ag.

For the fabricated device, the luminance was 14500 cd/m$^2$ (the voltage was 5V) and the EL efficiency was 9.7 cd/A.

EXAMPLE 26

A blue OLED was fabricated in the same manner as in Example 24, except using compound No. 17 as the host material and blue triplet dye Firpic as the dopant. The configuration of the device is: ITO/NPB(40 nm)/compound No. 17: Firpic (8%) (30 nm)/Bphen(30 nm)/Mg:Ag.

For the fabricated device, the luminance was 13500 cd/m$^2$(the voltage was 4.5V) and the EL efficiency was 10 cd/A.

EXAMPLE 27

A blue OLED was fabricated in the same manner as in Example 24, except using compound No.27 (CPF) as the host material and blue triplet dye Firpic as the dopant. The configuration of the device is: ITO/NPB(40 nm)/compound 27:Firpic (8%) (30 nm)/Bphen(30 nm)/Mg:Ag.

The performance of the fabricated device was: the emissive wavelength was at 472 nm, the luminance was 21100 cd/m$^2$(the voltage was 16.6V) and the EL efficiency was 11.4 cd/A (the current density was 8.3 A/m$^2$).

EXAMPLE 28

A green OLED was fabricated by using compound No. 20 (CPF) as the host material and blue triplet dye Ir(ppy)$_3$ as dopant. The fabrication includes: on an cleaned glass substrate coated with ITO, 40 nm NPB as the hole transport layer and 30 nm compound No. 20 doped with 6% (by weight) Ir(ppy)$_3$ as the emissive layer were deposited by a vacuum vapor deposition, then 30 nm hole blocking and electron transport layer Bphen and 200 nm metal of Mg:Ag (10:1) as cathode were deposited by a vacuum vapor deposition.

The configuration of the device is: ITO/NPB(40 nm)/compound20:Ir(ppy)$_3$ (8%) (30 nm)/Bphen(30 nm)/Mg:Ag.

The performance of the device was: the emissive wavelength was at 520 nm, the luminance was 11570 cd/m²(the voltage was 11V) and the EL efficiency was 30.5 cd/A (the current density was 8.5 A/m²).

EXAMPLE 29

A blue OLED was fabricated in the same manner as in Example 28, except using compound No. 33 as the host material and blue triplet dye Firpic as dopant. The configuration of the device is: ITO/NPB(40 nm)/compound No. 33:Firpic (8%) (30 nm)/Bphen(30 nm)/Mg:Ag.

For the fabricated device the luminance was 13500 cd/m² (the voltage was 4.5V) and the EL efficiency was 10 cd/A.

The foregoing specific examples are illustrative only and are not to be considered as limiting the invention, which is defined by the following claims. The technologists of this field should realize that any changes to these examples under the thought of the present invention would be included by the following claims.

What is claimed is:

1. A carbazole derivative represented by formula (III):

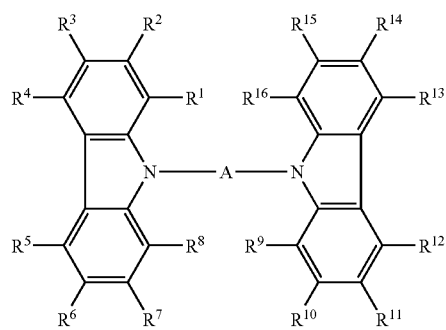

(formula III)

wherein Y is selected from two 6–50 carbon aromatic groups linked by a unit consisting of two 1–3 carbon alkyl groups linked by a 6–50 carbon aromatic group, alkyl groups linked to spiro groups, alkyl groups and aromatic groups linked to spiro groups, a group consisting of two 1–3 carbon alkyl groups linked by a unit of one or both of a fluorene moiety and a spiro moiety, and a group consisting of two 1–3 carbon alkyl groups linked by a nonplanar substituted or unsubstituted 6–50 carbon unit of one or both of a fluorene moiety and a spiro moiety, a group consisting of two 1–3 carbon alkyl groups linked by a unit consisting of two 6–50 carbon aromatic groups linked by an alkenyl group, and wherein $R^1$ to $R^{16}$ are independently selected from the group consisting of H, alkyl groups, alkoxy groups, aromatic groups, fluoroalkyl groups, halogens, and cyano.

2. The carbazole derivative according to claim 1, wherein the carbazole derivative has a glass transition temperature of between 70° C. and 220° C. and a triplet energy of 2.62 eV or more.

3. The carbazole derivative according to claim 1, wherein the derivative is selected from the group consisting of compounds according to any of the following formulae:

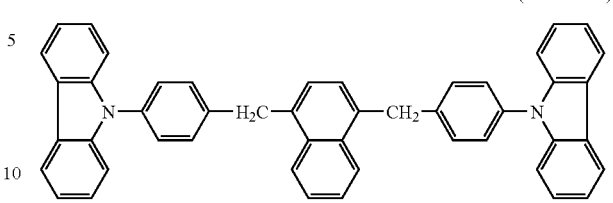

(formula 20)

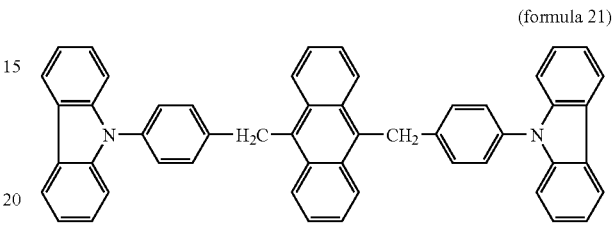

(formula 21)

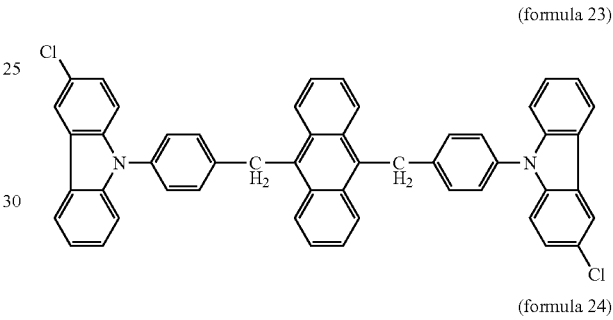

(formula 23)

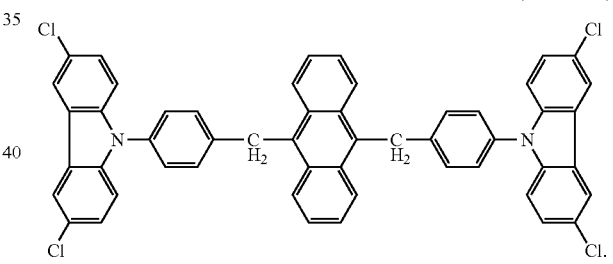

(formula 24)

4. The carbazole derivative according to claim 1, wherein Y consists of the group consisting of two 1–3 carbon alkyl groups linked by a unit consisting of two 6–50 carbon aromatic groups linked by an alkenyl group.

5. The carbazole derivative according to claim 4, wherein the derivative is represented by the formula 15:

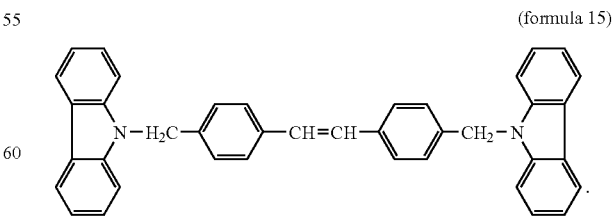

(formula 15)

6. The carbazole derivative according to claim 1, wherein the derivative is selected from the group consisting of compounds according to any of the following formulae:

(formula 13)
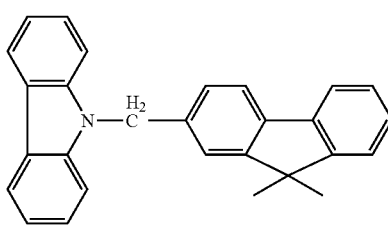
-continued
(formula 31)
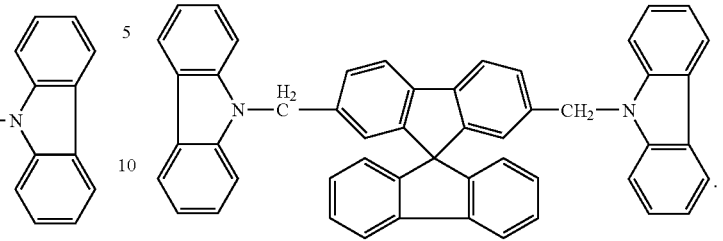
7. The carbazole derivative according to claim 1, wherein the derivative is selected from the group consisting compounds according to any of the following formulae:
(formula 14)
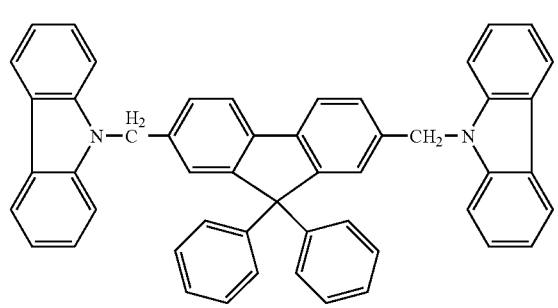
(formula 28)
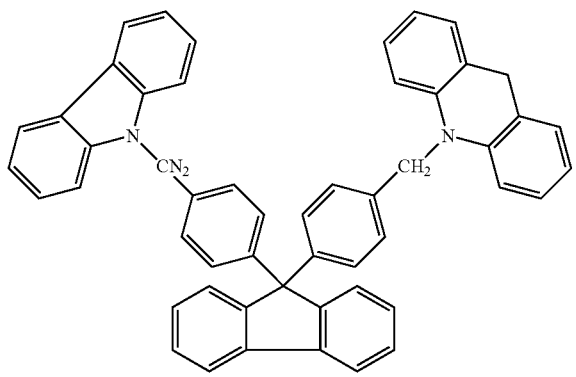
(formula 30)
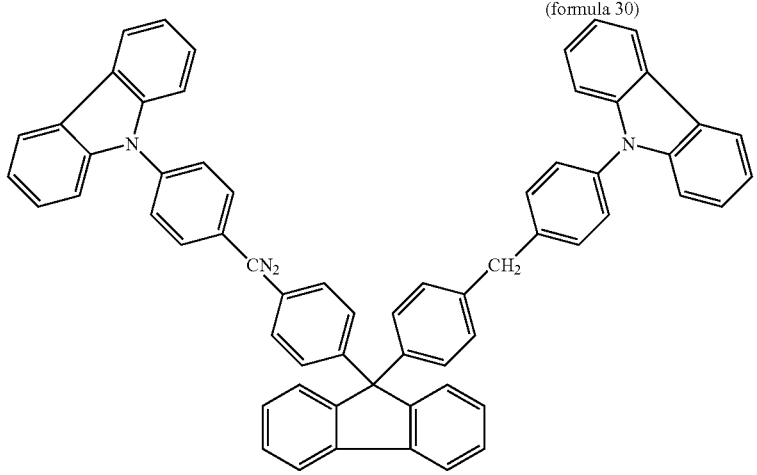

(formula 32)
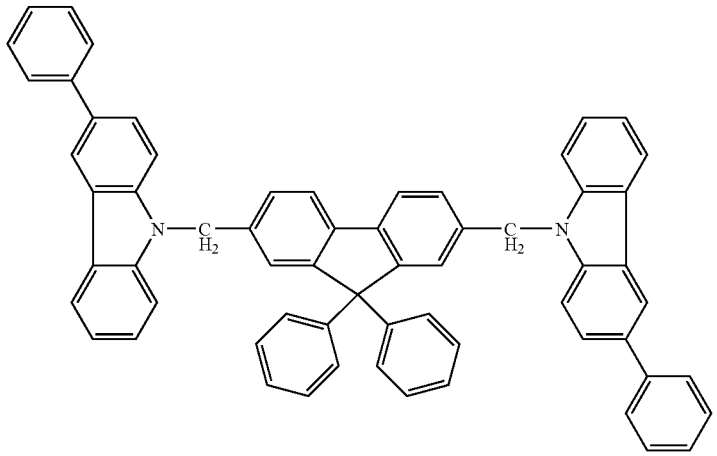
(formula 33)
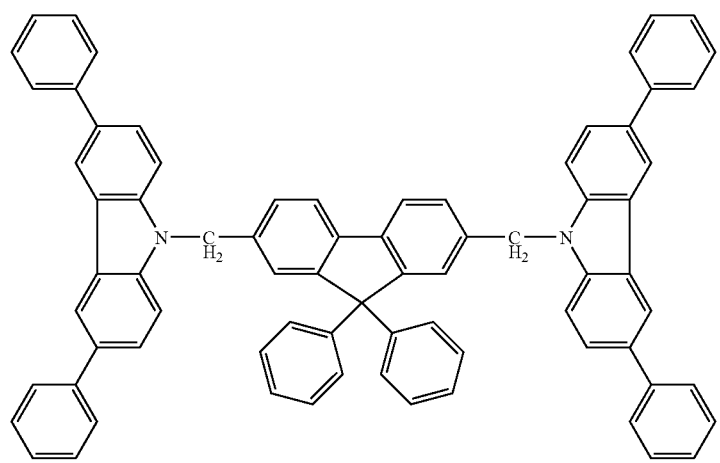
(formula 34)
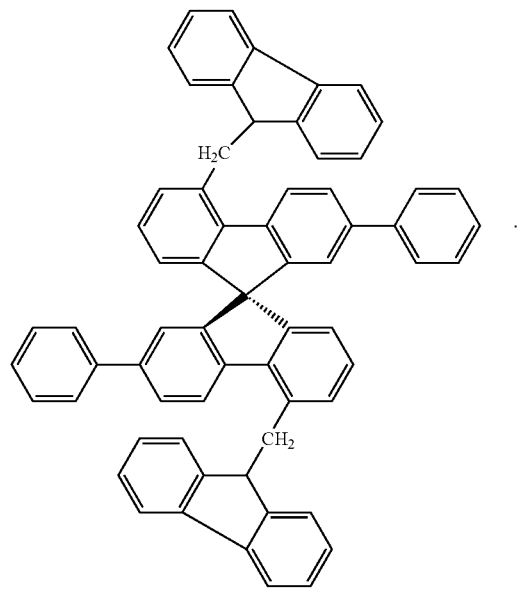

8. The carbazole derivative according to claim 1, wherein the unit comprises a spiro group that is substituted by one or more of an alkyl group, an aromatic group, and halogen.

9. The carbazole derivative according to claim 7, wherein the derivative is represented by formula 14:

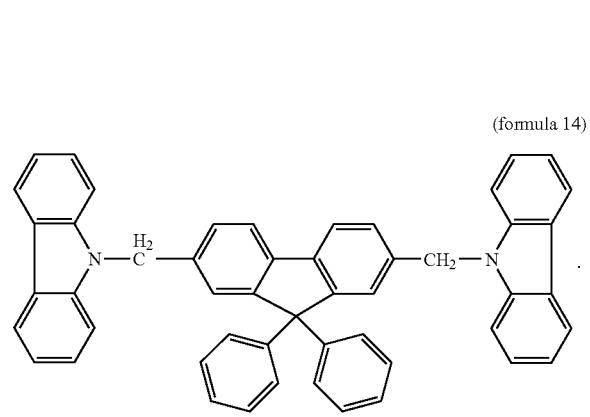

(formula 14)

10. The carbazole derivative according to claim 7, wherein the derivative is represented by formula 28:

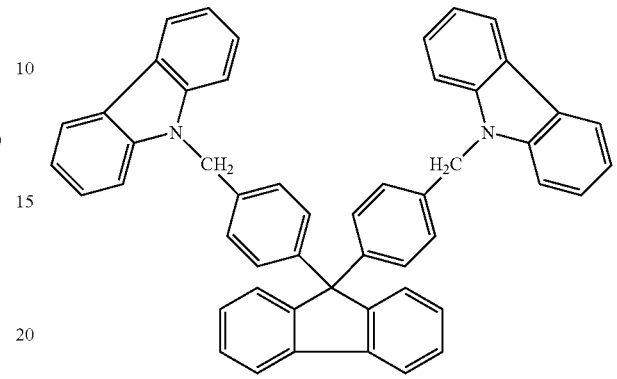

(formula 28)

11. The carbazole derivative according to claim 7, wherein the derivative is represented by formula 30:

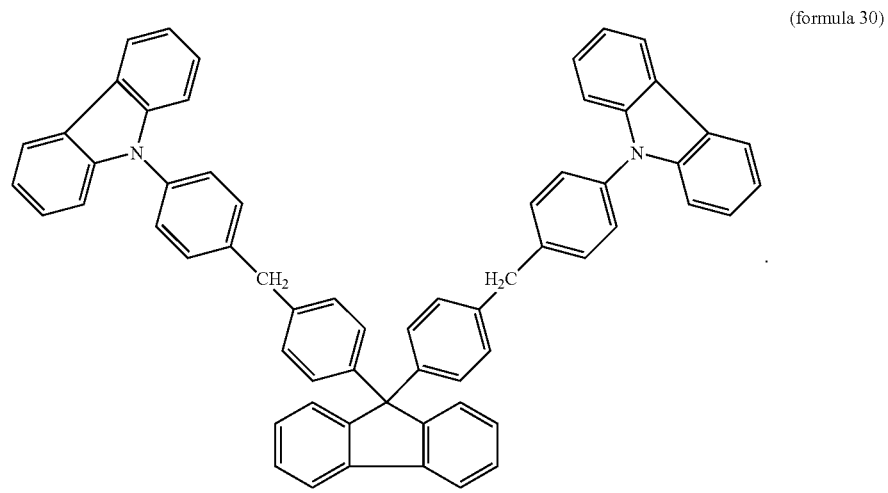

(formula 30)

12. A carbazole derivative represented by formula (22)

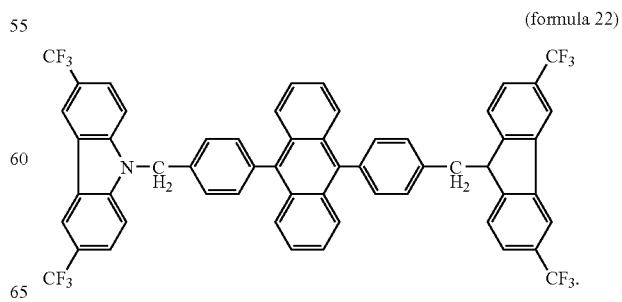

(formula 22)

13. The carbazole derivative represented by formula 25
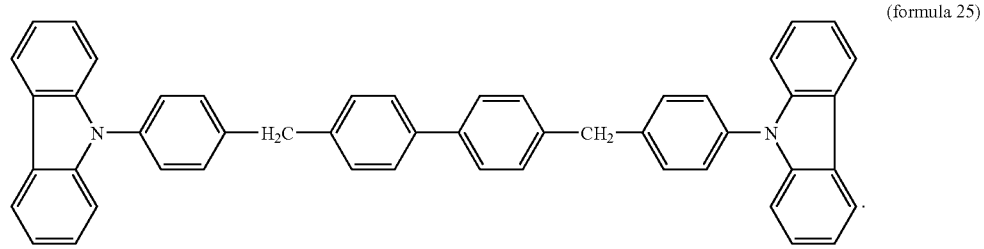
(formula 25)
14. The carbazole derivative represented by formula 26
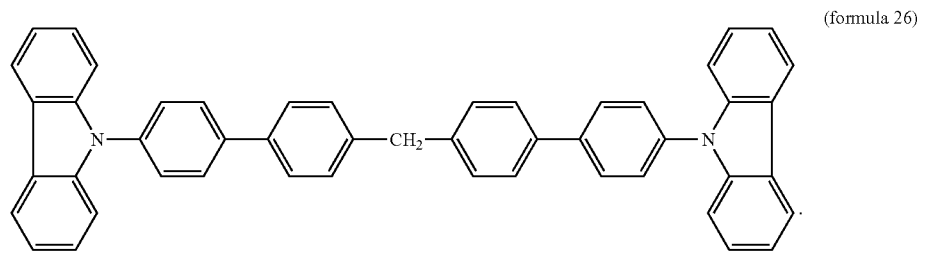
(formula 26)
15. The carbazole derivative represented by formula 27:
(formula 27)
* * * * *

UNITED STATES PATENT AND TRADEMARK OFFICE
CERTIFICATE OF CORRECTION

| | |
|---|---|
| PATENT NO. | : 7,227,027 B2 |
| APPLICATION NO. | : 10/933867 |
| DATED | : June 5, 2007 |
| INVENTOR(S) | : Yong Qi et al. |

It is certified that error appears in the above-identified patent and that said Letters Patent is hereby corrected as shown below:

On the Title page, at field (73),

"Assignees: Tsinghua University, Beijing (CH);
Beijing Visionox Technology Co., Ltd., Beijing (CH)"

should read:

--Assignees: Tsinghua University, Beijing (CN);
Beijing Visionox Technology Co., Ltd., Beijing (CN)--.

On the Title page, at field (56), under U.S. PATENT DOCUMENTS,

"6,670,054   B1      12/2003     Popovic et al. ............. 428/690"

should read:

--6,670,054   B1      12/2003     Hu et al. .....................428/690--.

UNITED STATES PATENT AND TRADEMARK OFFICE
CERTIFICATE OF CORRECTION

PATENT NO. : 7,227,027 B2 Page 2 of 7
APPLICATION NO. : 10/933867
DATED : June 5, 2007
INVENTOR(S) : Yong Qi et al.

It is certified that error appears in the above-identified patent and that said Letters Patent is hereby corrected as shown below:

At column 5,

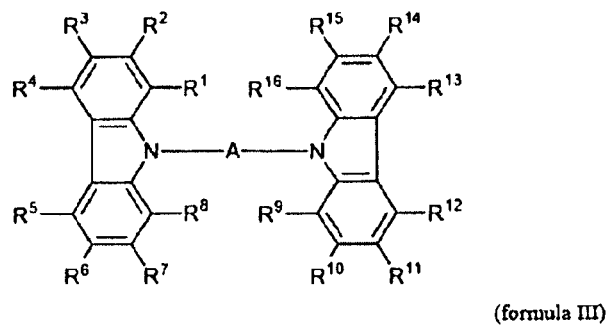

(formula III)

should be:

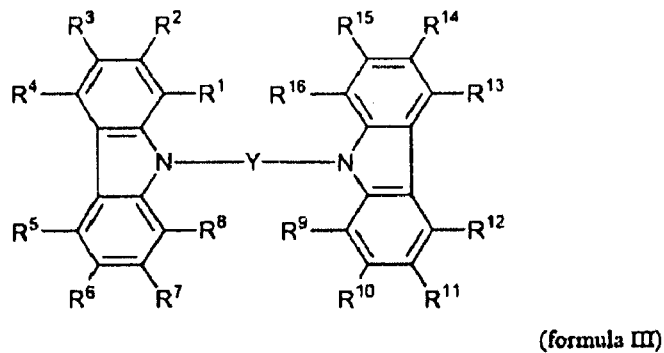

(formula III)

UNITED STATES PATENT AND TRADEMARK OFFICE
CERTIFICATE OF CORRECTION

PATENT NO. : 7,227,027 B2
APPLICATION NO. : 10/933867
DATED : June 5, 2007
INVENTOR(S) : Yong Qi et al.

It is certified that error appears in the above-identified patent and that said Letters Patent is hereby corrected as shown below:

At column 13,

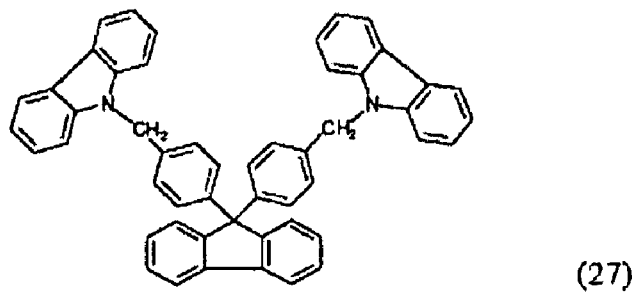

(27)

should be

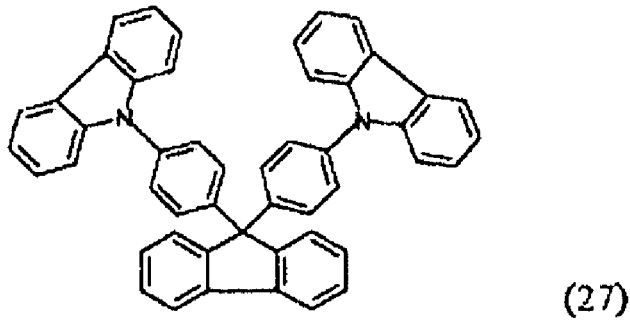

(27)

UNITED STATES PATENT AND TRADEMARK OFFICE
CERTIFICATE OF CORRECTION

PATENT NO. : 7,227,027 B2
APPLICATION NO. : 10/933867
DATED : June 5, 2007
INVENTOR(S) : Yong Qi et al.

It is certified that error appears in the above-identified patent and that said Letters Patent is hereby corrected as shown below:

At column 13,

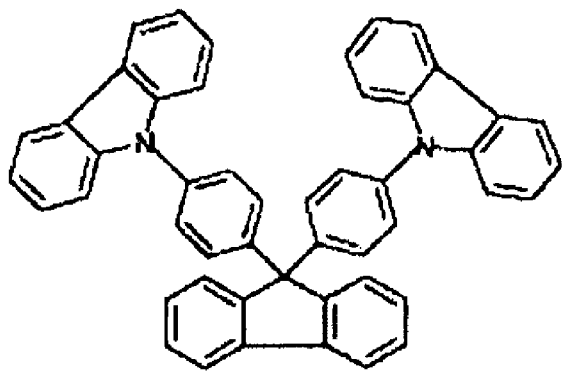

(28)

should be

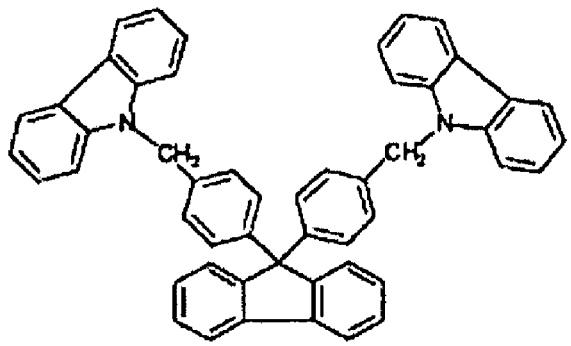

(28)

UNITED STATES PATENT AND TRADEMARK OFFICE
CERTIFICATE OF CORRECTION

PATENT NO. : 7,227,027 B2
APPLICATION NO. : 10/933867
DATED : June 5, 2007
INVENTOR(S) : Yong Qi et al.

It is certified that error appears in the above-identified patent and that said Letters Patent is hereby corrected as shown below:

At column 25,

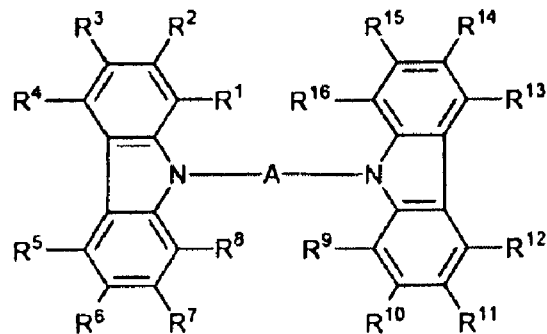

(formula III)

should be:

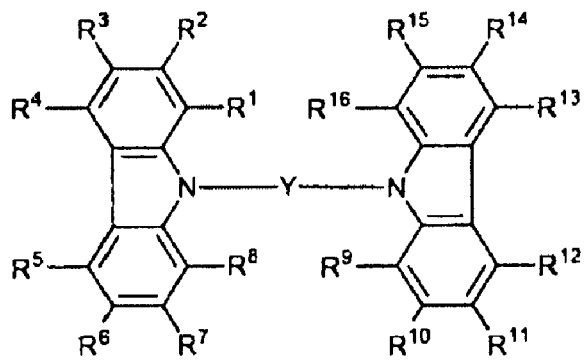

(formula III)

UNITED STATES PATENT AND TRADEMARK OFFICE
CERTIFICATE OF CORRECTION

PATENT NO.       : 7,227,027 B2
APPLICATION NO.  : 10/933867
DATED            : June 5, 2007
INVENTOR(S)      : Yong Qi et al.

It is certified that error appears in the above-identified patent and that said Letters Patent is hereby corrected as shown below:

At column 29,

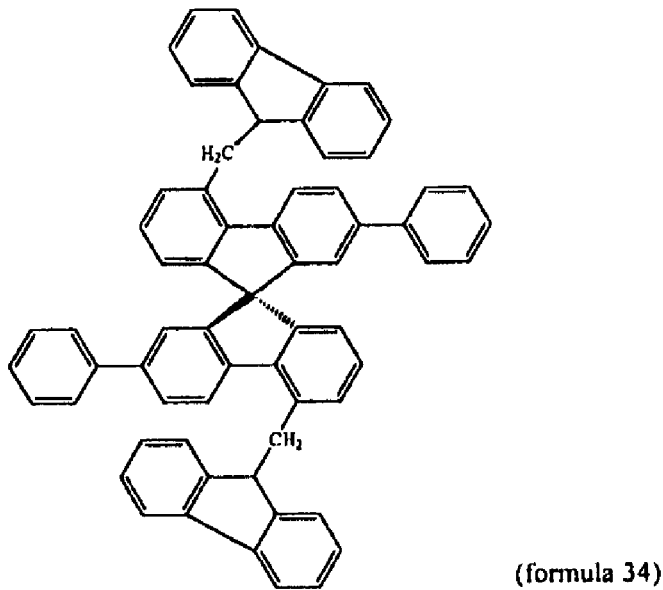

(formula 34)

UNITED STATES PATENT AND TRADEMARK OFFICE
CERTIFICATE OF CORRECTION

PATENT NO. : 7,227,027 B2
APPLICATION NO. : 10/933867
DATED : June 5, 2007
INVENTOR(S) : Yong Qi et al.

It is certified that error appears in the above-identified patent and that said Letters Patent is hereby corrected as shown below:

should be:

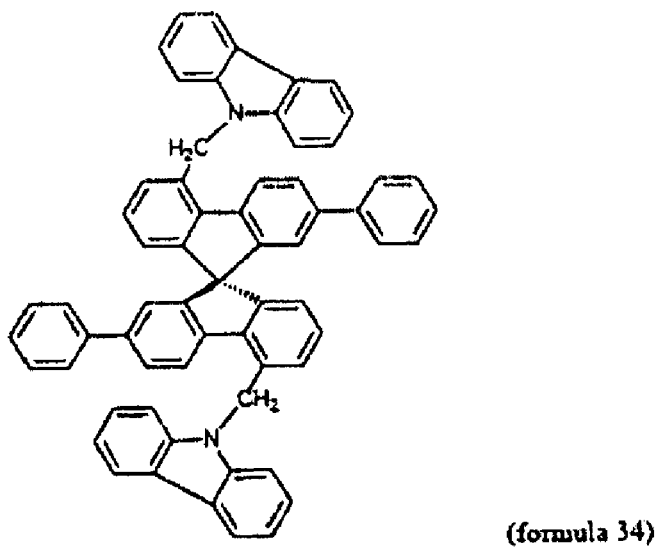

(formula 34)

Signed and Sealed this

Seventeenth Day of June, 2008

JON W. DUDAS
*Director of the United States Patent and Trademark Office*